US011826465B2

(12) United States Patent
Ray, II

(10) Patent No.: US 11,826,465 B2
(45) Date of Patent: Nov. 28, 2023

(54) NEBULIZATION FORMULATIONS FOR DELIVERY TO LOWER RESPIRATORY TRACT

(71) Applicant: CMPD Licensing, LLC, Conroe, TX (US)

(72) Inventor: Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

(21) Appl. No.: 17/740,790

(22) Filed: May 10, 2022

(65) Prior Publication Data

US 2023/0135537 A1 May 4, 2023

Related U.S. Application Data

(63) Continuation of application No. 17/513,759, filed on Oct. 28, 2021, now Pat. No. 11,324,694.

(51) Int. Cl.

| | |
|---|---|
| ***A61K 9/00*** | (2006.01) |
| ***A61K 47/26*** | (2006.01) |
| ***A61K 45/06*** | (2006.01) |
| ***A61K 47/12*** | (2006.01) |
| ***A61J 3/07*** | (2006.01) |
| ***A61K 31/135*** | (2006.01) |
| ***A61K 31/439*** | (2006.01) |
| ***A61K 31/522*** | (2006.01) |
| ***A61K 33/30*** | (2006.01) |
| ***A61K 31/197*** | (2006.01) |

(52) U.S. Cl.

CPC ............. *A61K 9/0078* (2013.01); *A61J 3/078* (2013.01); *A61K 31/135* (2013.01); *A61K 31/197* (2013.01); *A61K 31/439* (2013.01); *A61K 31/522* (2013.01); *A61K 33/30* (2013.01); *A61K 45/06* (2013.01); *A61K 47/12* (2013.01); *A61K 47/26* (2013.01)

(58) Field of Classification Search

None

See application file for complete search history.

(56) References Cited

U.S. PATENT DOCUMENTS

2002/0183292 A1* 12/2002 Pairet ...................... A61P 29/00 514/291
2005/0201951 A1* 9/2005 Barr ..................... A61K 9/0073 514/20.3

OTHER PUBLICATIONS

Pharmapproach, In-Process Quality Control (IPQC) of Pharmaceutical Dosage Forms, Pharmaceutical Technology, Sep. 29, 2020). (Year: 2020).*
Cazzola et al. (Influence of N-acetylcysteine on chronic bronchitis or COPD exacerbations: a meta-analysis, European Respiratory Review, 2015). (Year: 2015).*
Pharmaceutical Guidelines (Various Types of Blenders and Their Purposes, posted online Apr. 20, 2017). (Year: 2017).*
Pharmaceutical Guidelines (Various Types of Blenders and Their Purposes), Apr. 20, 2017.

* cited by examiner

*Primary Examiner* — Melissa S Mercier
(74) *Attorney, Agent, or Firm* — Akerman LLP

(57) ABSTRACT

A method of making a pharmaceutical composition for delivery to the lower respiratory tract via nebulization within a sterile diluent includes mixing dry powder ingredients including a beta agonist or anticholinergic and one or more additional ingredients to formulate a dry powder mixture for mixing with the sterile diluent.

24 Claims, No Drawings

NEBULIZATION FORMULATIONS FOR DELIVERY TO LOWER RESPIRATORY TRACT

CROSS-REFERENCE TO RELATED APPLICATIONS

The present application is a continuation of U.S. patent application Ser. No. 17/513,759, filed Oct. 28, 2021, the contents of which are hereby incorporated by reference in their entirety.

FIELD OF THE TECHNOLOGY

The present disclosure is directed to nebulization formulations for delivery to the lower respiratory tract.

BACKGROUND

Respiratory tract conditions are extremely common ailments of the human experience and include rhinologic conditions, infections, and other obstructions to respiration. One reason for this frequency is constant exposure of respiratory surfaces to the external environment. For example, foreign matter such as debris, microorganisms, viruses, biological matter, and even harsh environmental conditions may enter the body during respiration, irritating or infecting respiratory tract surfaces or even the internal body. Overtime, the human body has also evolved defenses designed to protect the body from this exposure. These defenses include mucous lining and immune responses such as inflammation and increased mucous production or viscosity. Diseases and abnormalities such as chronic obstructive pulmonary disease (COPD), asthma, rhinitis, and various allergies may also include undesirable triggering or modulation of such defenses, e.g., excessive immune responses that cause bronchoconstriction or excessive mucous production or thickening.

Often times an initial treatment objective of respiratory tract conditions is to relieve the obstruction and restore unobstructed respiration by increasing drainage or relieving inflammation. Further objectives may be directed to relieving discomfort or treating the underlying condition. Treatments may include localized application or action of medications, e.g., using nasal spray or metered inhaler. However, respiratory tract conditions may manifest at multiple locations complicating targeted delivery of medication where needed, thus, systemic delivery routes such as oral or intravenous administration, have also been used. Causes of respiratory tract conditions are also numerous and identification of a precise cause may be difficult, especially when multiple conditions are present. What are needed are additional formulations and treatments to treat respiratory tract conditions for delivery to the lower respiratory tract.

SUMMARY

In one aspect, a method of making a pharmaceutical composition for delivery to the lower respiratory tract via nebulization within a sterile diluent includes mixing dry powder ingredients to formulate a dry powder mixture. The dry powder ingredients may include a first ingredient comprising a beta agonist or an anticholinergic and a second ingredient comprising one or more additional active ingredients comprising one or more pharmaceutical drugs, one or more inactive ingredients, or combination thereof.

In one example, the method includes enclosing the dry powder mixture within a capsule, satchel, or other pharmaceutical container.

In a further or another example, the method includes preparing an aliquot of the dry powder mixture and analyzing the aliquot for accurate mixing and final concentration of ingredients.

In any of the above or another example, mixing the dry powder ingredients to formulate the dry powder mixture includes mixing the dry powder ingredients with a motorized mixing device.

In any of the above or another example, the second ingredient comprises xylitol, poloxamers, or both.

In any of the above or another example, the first ingredient is the beta agonist, and the beta agonist is selected from levalbuterol or albuterol.

In a further example, the levalbuterol or albuterol is mixed at a unit dose amount of about 0.5 mg to about 2.5 mg for each unit dose in the dry powder mixture.

In a further example, the second ingredient comprises the one or more additional active ingredients, and the one or more additional active ingredients comprise a mucolytic.

In a further example, the mucolytic is acetylcysteine.

In a further example, the second ingredient further comprises the one or more inactive ingredients comprising xylitol, poloxamers, or both.

In one example, the first ingredient is the anticholinergic, and wherein the anticholinergic is ipratropium.

In a further example, the ipratropium is mixed at a unit dose amount of about 0.1 mg to about 1.0 mg for each unit dose in the dry powder mixture.

In a further example, the second ingredient comprises the one or more additional active ingredients comprising a mucolytic.

In a further example, the mucolytic is acetylcysteine.

In a further example, the second ingredient further comprises the one or more inactive ingredients comprising xylitol, poloxamers, or both.

In another aspect, a method of delivering a pharmaceutical composition to the lower respiratory tract includes combining a dry powder with a sterile diluent to formulate a solution or suspension; and nebulizing the solution or suspension to generate particles, wherein the dry powder comprises a beta agonist or an anticholinergic.

In one example, the sterile diluent is a sterile aqueous diluent.

In a further example, the dry powder includes the beta agonist is selected from levalbuterol or albuterol in a unit dose amount of about 0.5 mg to about 2.5 mg.

In a further or another example, the dry powder includes the anticholinergic comprising ipratropium in a unit dose amount of about 0.1 mg to about 1.0 mg.

In any of the above or another example, the dry powder further includes xylitol or poloxamers.

In any of the above or another example, the dry powder includes a mucolytic comprising acetylcysteine in a unit dose amount of about 0.5 mg to about 100 mg.

In any of the above or another example, the dry powder further includes: one or more steroids in a unit dose amount of about 0.01 mg to about 8 mg; one or more antihistamines in a unit dose amount of about 0.1 mg to about 50 mg; theophylline in a unit dose amount of about 1 mg to about 100 mg; sodium citrate in a unit dose amount of about 0.5 mg to about 100 mg; zinc in a unit dose amount of about 0.5 mg to about 30 mg; one or more antifungal drugs in a unit dose amount of about 0.1 mg to about 100 mg; one or more antibiotics in a unit dose amount of about 0.5 mg to about 100 mg; one or more antiviral drugs in a unit dose amount of about 0.1 mg to about 50 mg; one or more anti-inflammatory drugs in a unit dose amount of about 0.1 mg to about 60 mg; one or more leukotriene receptor antagonists in a unit dose amount of about 0.01 mg to about 20 mg; quinine sulfate in a unit dose amount of about 0.5 mg to about 100 mg; or combination thereof.

DESCRIPTION

The present disclosure describes compositions and related methods of treating, e.g., managing, conditions associated with the respiratory tract for delivery to the lower respiratory tract. In some embodiments, the compositions may include antimicrobials and/or other actives or inactives to combat infection or symptoms arising from an infection of the lower respiratory tract or condition affecting the lower respiratory tract, such as bronchitis, pneumonia, tuberculosis. In some embodiments, the compositions may be used to treat non-infective conditions or symptoms arising from non-infective conditions related to the lower respiratory tract such as chronic obstructive pulmonary disease or asthma.

The compositions may typically be provided in a dry powder comprising or consisting of one or more active ingredients. In some formulations, the dry powder may be mixed with a diluent prior to administration. Administration may be via nebulization to the lower respiratory tract. The diluent may be an aqueous diluent and will typically be sterile.

In some embodiments, a topical composition disclosed herein may be used as a supplemental or replacement therapy for patients who are currently using nasally delivered steroids, nasally or orally delivered antihistamines, nasally delivered anticholinergics, nasally or orally delivered mucolytics, orally delivered montelukast, or irrigation systems to clear out the nasal cavities and remove debris.

The topical composition and associated methods of treatment may include a pharmaceutically effective amount of an active component, which those having skill in the art will appreciate may include salts, pharmaceutical equivalents, or derivatives thereof. For brevity, however, such salts, equivalents, and derivatives may be referred to herein with respect to the active agent or class of active agent. For example, the composition may comprise albuterol, which is intended to encompass equivalent pharmaceutical salts or derivatives, such as an effective amount of albuterol sulfate.

Embodiments of the composition may include various ingredients including active agents, inactive agents, bases, carriers, excipients, solubilization agents, dispersion agents, emulsifiers, diluents, flavoring agents, pH adjusting agents, fillers, or the like.

Various embodiments of the composition may include an active component selected from a beta agonist, anticholinergic, or combination thereof. In a further example, the composition may include one or more of a steroid, antihistamine, mucolytic, antimicrobial, zinc, or combinations thereof.

In some embodiments, the composition includes an active ingredient comprising or consisting of one or more beta agonists. In one example, the beta agonist may include one or more beta agonists selected from albuterol, arformoterol, buphenine, clenbuterol, dopexamine, epinephrine, fenoterol, formoterol, isoetarine, isoprenaline, isoproterenol, levosalbutamol, levalbuterol, orciprenaline, metaproterenol, pirbuterol, procaterol, ritodrine, salbutamol, salmeterol, terbutaline, or combination thereof. A unit dose of the composition may include the beta agonist in an amount about 0.45 mg to about 3 mg, such as about 0.5 mg to about 2.5 mg, about 0.5 mg to about 2 mg, about 0.5 mg to about 1.5 mg, about 0.5 mg to about 1 mg, about 1 mg to about 2.5 mg, about 1 mg to about 2 mg, about 1.5 mg to about 2.5 mg, greater than 1 mg, greater than 1.5 mg, or greater than 2 mg.

The composition including one or more beta agonists may include one or more active or inactive ingredients, such as those described herein. For example, in various embodiments, the composition includes any of the beta agonist identified above or elsewhere herein, in an amount described above or elsewhere herein, wherein the active ingredient further includes one or more of a steroid, mucolytic, antihistamine, theophylline, sodium citrate, zinc, antifungal drug, antibiotic, antiviral, anti-inflammatory, leukotriene receptor antagonist, or quinine sulfate or any combination thereof, including any of such active ingredients identified herein, in any amount or range described herein.

In some embodiments, the composition includes an active ingredient comprising or consisting of one or more anticholinergics. In one example, the anticholinergic may include one or more anticholinergics selected from atropine, belladonna alkaloids, benztropine mesylate, clidinium, cyclopentolate, darifenacin, dicylomine, fesoterodine, flavoxate, glycopyrrolate, homatropine hydrobromide, yoscyamine, ipratropium (e.g., ipratropium bromide), orphenadrine, oxitropium, oxybutynin, propantheline, propantheline bromide, scopolamine, methscopolamine, solifenacin, tiotropium, tolterodine, trihexyphenidyl, trospium, or combination thereof.

A unit dose of the composition may include the anticholinergic in an amount about 0.01 mg to about 1 mg, about 0.01 mg to about 0.1 mg, about 0.02 mg to about 0.1 mg, about 0.03 mg to about 0.1 mg, about 0.05 mg to about 0.6 mg, about 0.08 mg to about 0.5 mg, about 0.1 to about 0.5 mg, or about 0.5 mg to about 1 mg. In one embodiment, the anticholinergic comprises ipratropium in a unit dose amount about 0.1 mg to about 1 mg, such as about 0.1 to about 0.5 mg, about 0.25 mg to about 0.75 mg, about 0.25 mg to about 1 mg.

The composition including one or more anticholinergics may include one or more active or inactive ingredients, such as those described herein. For example, in various embodiments, the composition includes any of the anticholinergics identified above or elsewhere herein, in an amount described above or elsewhere herein, wherein the active ingredient further includes one or more of a steroid, mucolytic, antihistamine, theophylline, sodium citrate, zinc, antifungal drug, antibiotic, antiviral, anti-inflammatory, leukotriene receptor antagonist, or quinine sulfate or any combination thereof, including any of such active ingredients identified herein, in any amount or range described herein.

In various embodiments, the composition includes an active ingredient comprising or consisting of one or both of a beta agonist or an anticholinergic and a mucolytic. Mucolytics may be present to assist in dissolving or breaking down mucus in the respiratory tract. Accordingly, in one embodiment, the composition includes one or more mucolytics selected from acetylcysteine, erdosteine, bromheksin, carbocisteine and guaifenesin or pharmaceutically acceptable salts thereof. A unit dose of the composition may include the mucolytic in an amount about 0.5 mg to about 500 mg, such as about 0.5 mg to about 5 mg, about 5 mg to about 15 mg, about 15 mg to about 100 mg, about 50 mg to about 150 mg, about 75 mg to about 200 mg, about 75 mg to about 150 mg, about 100 mg to about 250 mg, about 200 mg to about 500 mg. In one embodiment, the mucolytic comprises acetylcysteine in a unit dose amount about 0.5 mg to about 250 mg, about 15 mg to about 250 mg, about 25 mg to about 200 mg, about 50 mg to about 150 mg, about 75 mg to about 125 mg, or about 100 mg.

In various embodiments, the composition includes an active ingredient comprising or consisting of one or both of a beta agonist or an anticholinergic and one or more of a steroid or a mucolytic. One or more steroids of an active ingredient may include a corticosteroid, glucocorticoid steroid, or both, for example. Corticosteroids mimic the effects of hormones that the body produces naturally in your adrenal glands. Corticosteroids can suppress inflammation and can reduce the signs and symptoms of inflammatory conditions (e.g., arthritis and asthma). Corticosteroids can also suppress the immune system. Corticosteroids can act on a number of different cells (e.g., mast cells, neutrophils, macrophages and lymphocytes) and a number of different mediators (e.g., histamine, leukotriene, and cytokine subtypes). In various embodiments, the composition include one or more steroids selected from triamcinolone (e.g., diacetate, hexacetonide, and acetonide), betamethasone (e.g., dipropionate, benzoate, sodium phosphate, acetate, and valerate), dexamethasone (e.g., dipropionate and valerate), flunisolide, prednisone (e.g., acetate), prednisolone (e.g., acetate, sodium phosphate, and tebutate), methylprednisolone (e.g., acetate and sodium succinate), fluocinolone (e.g., acetonide), budesonide, diflorasone (e.g., diacetate), halcinonide, desoximetasone (desoxymethasone), diflucortolone (e.g., valerate), flucloronide (fluocortolone acetonide), fluocinonide, fluocortolone, fluprednidene (e.g., acetate), flurandrenolide (flurandrenolone), clobetasol (e.g., propionate), clobetasone (e.g., butyrate), alclometasone, flumethasone (e.g., pivalate), fluocortolone (e.g., hexanoate), amcinonide, beclomethasone (e.g., dipropionate), fluticasone (e.g., propionate), difluprednate, prednicarbate, flurandrenolide, mometasone, desonide, or combination thereof.

A unit dose of the composition may include the steroid in an amount about 0.25 mg to about 10 mg, such as about 0.5 mg to about 8 mg, about 1 mg to about 6 mg, about 2 mg to about 5 mg, about 3 mg to about 5 mg, about 4 mg to about 6 mg, about 5 mg to about 7 mg, about 6 mg to about 9 mg, about 6 mg to about 10 mg, about 0.25 mg to about 5 mg, about 0.5 mg to about 5 mg, about 0.5 mg to about 3 mg, about 0.5 to about 2 mg, about 2 mg to about 3 mg, about 3 mg to about 4 mg, about 0.25 mg, about 0.5 mg, about 1 mg, about 2 mg, about 3 mg, about 4 mg, about 5 mg, about 6 mg, or about 7 mg. In one embodiment, the steroid comprises or consists of fluticasone. For example, a unit dose of the composition may include fluticasone in an amount about 0.5 mg to about 6 mg, about 1 mg to about 5 mg, about 2 mg to about 4 mg, about 2 mg to about 3 mg, about 3 mg to about 4 mg, or about 3 mg. In one embodiment, the steroid comprises or consists of budesonide. For example, a unit dose of the composition may include budesonide in a unit dose amount about 0.25 mg to about 4 mg, about 0.25 mg to about 3 mg, about 0.25 mg to about 2 mg, about 0.5 mg to about 2 mg, about 0.5 to about 1 mg, about 1 mg to about 2 mg, about 0.5 mg, about 1 mg, or about 2 mg. In one embodiment, the steroid comprises or consists of methylprednisolone. For example, a unit dose of the composition may include methylprednisolone in a unit dose amount about 1 mg to about 10 mg, about 2 mg to about 9 mg, about 3 mg to about 8 mg, about 4 mg to about 7 mg, about 4 mg to about 6 mg, about 4 mg to about 5 mg, about 4 mg, about 5 mg, about 6 mg, or about 8 mg.

In various embodiments, the composition includes an active ingredient comprising or consisting of one or both of a beta agonist or an anticholinergic and one or more of a steroid, mucolytic, or antihistamine. The antihistamine may include one or more antihistamines. Antihistamines act to reduce or block histamine receptors (e.g., H1 receptors and H2 receptors) selected from acrivastine, azelastine, bilastine, bromodiphenhydramine, brompheniramine, buclizine, carbinoxamine, cetirizine, chlorodiphenhydramine, chlorphenamine, chlorpheniramine, chlorpromazine, cimetidine, clemastine, cyclizine, cyproheptadine, desloratadine, dexbrompheniramine, dexchlorpheniramine, dimenhydrinate, dimetindene, diphenhydramine, doxylamine, ebastine, embramine, emedastine, famotidine, fexofenadine, hydroxyzine, lafutidine, levocabastine, loratadine, meclozine, mirtazapine, nizatidine, olopatadine, orphenadrine, phenindamine, pheniramine, phenyltoloxamine, promethazine, pyrilamine, quetiapine, ranitidine, roxatidine, rupatadine, tiotidine, tripelennamine, or triprolidine. A unit dose of the composition may include the antihistamine in an amount about 1 mg to about 1 g, about 2 mg to about 100 mg, about 15 mg to about 300 mg, about 25 mg to about 300 mg, about 50 mg to about 250 mg, about 75 mg to about 200 mg, about 100 mg to about 900 mg, about 200 mg to about 800 mg, about 300 mg to about 700 mg, about 400 mg to about 700 mg, or about 500 mg to about 800 mg. In one embodiment, the antihistamine comprises or consists of azelastine in an amount about 1 mg to 1000 mg, about 1 mg to about 50 mg, about 10 mg to about 100 mg, about 200 mg to about 900 mg, 300 mg to about 800 mg, 400 mg to about 700 mg, 400 mg to about 600 mg, 500 mg to about 600 mg, about 400 mg, about 500 mg, or about 500 mg.

In various embodiments, the composition includes an active ingredient comprising or consisting of one or both of a beta agonist or an anticholinergic and one or more of a steroid, mucolytic, antihistamine, or theophylline. A unit dose of the composition may include theophylline in an amount about 1 mg to about 250 mg, 1 mg to about 20 mg, about 25 mg to about 200 mg, about 50 mg to about 150 mg, about 75 mg to about 125 mg, or about 100 mg.

In various embodiments, the composition includes an active ingredient comprising or consisting of one or both of a beta agonist or an anticholinergic and one or more of a steroid, mucolytic, antihistamine, theophylline, or sodium citrate. Sodium citrate may include monosodium citrate, disodium citrate, or preferably trisodium citrate or more preferably sodium citrate dihydrate. A unit dose of the composition may include sodium citrate in an amount about 1 mg to about 150 mg, such as about 5 mg to about 150 mg, about 10 mg to about 100 mg, about 10 mg to about 75 mg, about 25 mg to about 50 mg, about 50 mg to about 75 mg, about 50 mg to about 100 mg, or about 75 mg to about 100 mg.

In various embodiments, the composition includes an active ingredient comprising or consisting of one or both of a beta agonist or an anticholinergic and one or more of a steroid, mucolytic, antihistamine, theophylline, sodium citrate, or zinc. The zinc may be or include zinc citrate, zinc HCl, another suitable zinc salt, or combination thereof. A unit dose of the composition may comprise zinc in an amount about 1 mg to about 30 mg, such as about 1 mg to about 20 mg, about 1 mg to about 15 mg, about 1 mg to about 6 mg, about 5 mg to about 30 mg, about 5 mg to about 20 mg, about 5 mg to about 15 mg, about 10 mg to about 30 mg, about 10 mg to about 25 mg, about 10 mg to about 20 mg, about 15 mg to about 30 mg, about 15 mg to about 25 mg, about 15 mg to about 20 mg, about 20 to about 30 mg, about 20 mg to about 25 mg, about 25 mg to about 30 mg, about 5 mg, about 10 mg, about 15 mg, about 20 mg, about 25 mg, or about 30 mg. In one embodiment, a unit dose of the composition comprises zinc in an amount greater than about 5 mg, greater than about 10 mg, greater than about 15 mg, greater than about 20 mg, greater than about 25 mg, or greater than about 30 mg.

In various embodiments, the composition includes an active ingredient comprising or consisting of one or both of a beta agonist or an anticholinergic and one or more of a steroid, mucolytic, antihistamine, theophylline, sodium citrate, zinc, or antifungal drugs. Antifungal drugs may include an antifungal selected from one or more categories of antifungals including azoles (imidazoles), antimetabolites, allylamines, morpholine, glucan synthesis inhibitors (echinocandins), polyenes, benoxaaborale; other antifungal/onychomycosis agents, and new classes of antifungal/onychomycosis agents. For example, the antifungal may comprise or consist of one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In some embodiments, the antifungal is selected from one or more azoles. In one embodiment, the antifungal is selected from itraconazole, voriconazole, or combination thereof. A unit dose of the composition may comprise the antifungal in an amount about 1 mg to about 1 g, such as about 1 mg to about 50 mg, about 50 mg to about 200 mg, about 100 mg to about 400 mg, about 200 mg to about 500 mg, about 50 mg or less, about 50 mg or greater, about 100 mg or greater, about 150 mg or greater, about 200 mg or greater, about 300 mg or greater, about 400 mg or greater, about 500 mg or greater, about 600 mg or greater.

In various embodiments, the composition includes an active ingredient comprising or consisting of one or both of a beta agonist or an anticholinergic and one or more of a steroid, mucolytic, antihistamine, theophylline, sodium citrate, zinc, antifungal drug, or antibiotic. The antibiotic may include one or more antibiotics selected from enicillins, cephalosporins, fluoroquinolones, aminoglycosides, monobactams, carbapenems, macrolides, other antibiotics, or combination thereof. For example, the antibiotic may include one or more antibiotics selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, meticillin, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In some embodiments, the antibiotic is selected from mupirocin, gentamycin, tobramycin, or combinations thereof. In one embodiment, the antibiotic includes an aminoglycoside. A unit dose of the composition may comprise the antibiotic in an amount about 1 mg to about 1 g, such as about 1 mg to about 50 mg, about 50 mg to about 200 mg, about 100 mg to about 400 mg, about 200 mg to about 500 mg, about 50 mg or less, about 50 mg or greater, about 100 mg or greater, about 150 mg or greater, about 200 mg or greater, about 300 mg or greater, about 400 mg or greater, about 500 mg or greater, about 600 mg or greater.

In various embodiments, the composition includes an active ingredient comprising or consisting of one or both of a beta agonist or an anticholinergic and one or more of a steroid, mucolytic, antihistamine, theophylline, sodium citrate, zinc, antifungal drug, antibiotic, or antiviral. The antiviral may include one or more antivirals selected from acyclovir, famciclovir, valacyclovir, penciclovir, or combinations thereof. A unit dose of the composition may comprise the antiviral in an amount about 1 mg to about 200 mg, such as about 1 mg to about 50 mg, about 1 mg to about 10 mg, about 20 mg to about 80 mg, about 50 mg to about 100 mg, about 75 mg to about 150 mg, at least about 3 mg, at least about 7 mg, at least about 15 mg, at least about 50 mg, or at least about 75 mg.

In various embodiments, the composition includes an active ingredient comprising or consisting of one or both of a beta agonist or an anticholinergic and one or more of a steroid, mucolytic, antihistamine, theophylline, sodium citrate, zinc, antifungal drug, antibiotic, antiviral, or anti-inflammatory. The anti-inflammatory may include one or more anti-inflammatories selected from may comprise or consist of hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide, or non-steroidal anti-inflammatories (NSAIDs) such as salicylate, indomethacin, ibuprofen, diclofenac, flurbiprofen, piroxicam indomethacin, ibuprofen, naxopren, piroxicam or nabumetone. A unit dose of the composition may comprise the anti-inflammatory in an amount about 1 mg to about 60 mg, such as about 1 mg to about 50 mg, about 1 mg to about 40 mg, about 1 mg to about 30 mg, about 1 mg to about 30 mg, about 1 mg to about 20 mg, about 1 mg to about 10 mg, about 5 mg to about 15 mg, about 10 mg to about 25 mg, about 20 mg to about 40 mg, about 25 mg to about 50 mg, greater than about 5 mg, greater than about 10 mg, greater than about 15 mg, greater than about 20 mg, greater than about 25 mg, or greater than 30 mg.

In various embodiments, the composition includes an active ingredient comprising or consisting of one or both of a beta agonist or an anticholinergic and one or more of a steroid, mucolytic, antihistamine, theophylline, sodium citrate, zinc, antifungal drug, antibiotic, antiviral, anti-inflammatory, or leukotriene receptor antagonists. The leukotriene receptor antagonist may be selected from one or more of montelukast, zafirlukast, zileuton, or a combination thereof. A unit dose of the composition may include about 0.01 mg to about 20 mg leukotriene receptor antagonist, such as about 0.5 mg to about 3 mg, about 3 mg to about 10 mg, about 5 mg to about 15 mg, greater than 0.5 mg, greater than 1.5 mg, greater than 3 mg, or greater than 5 mg.

In various embodiments, the composition includes an active ingredient comprising or consisting of one or both of a beta agonist or an anticholinergic and one or more of a steroid, mucolytic, antihistamine, theophylline, sodium citrate, zinc, antifungal drug, antibiotic, antiviral, anti-inflammatory, leukotriene receptor antagonist, or quinine sulfate. The quinine sulfate may include equivalent amounts of active substance from quinine or other quinine salts such as quinine hydrochloride, quinine di-hydrochloride, quinine sulfate dehydrate, quinine bisulfate, or quinine gluconate. A unit dose of the composition may include quinine sulfate in an amount about 1 mg to about 150 mg, about 50 mg to about 1000 mg, about 50 mg to about 700 mg, about 100 mg to about 700 mg, about 200 mg to about 500 mg, about 300 mg to about 400 mg, about 300 mg to about 700 mg, about 400 mg to about 700 mg, about 500 mg to about 700 mg, about 600 mg to about 700 mg, or about 325 mg or about 650 mg.

In various embodiments, the composition may include one or more inactive ingredients in addition to one or more active ingredients, such as those described herein. Inactive ingredients may include, for example, excipients, diluents, or carriers. In some formulations, inactive ingredients may be synthetic or naturally derived ingredients such as one or more of a base, solvent, surfactant, permeation enhancer, emollient, pH modifying agent, buffer, solubility enhancer, or a carrier molecule or complex configured to enhance or modulate diffusion, localization, targeting, active or passive transport, or uptake, for example, of one or more active agents. Other inactives may include solvents, preservatives, flavorings, stabilizers (including antioxidants), colorants, sorbents, glidents, fillers, or bulking agents. When included alone or together with active ingredients in a dry powder format, the inactive ingredients may similarly be provided in a dry powder.

In some embodiments, the composition includes inactive ingredients including one or both of xylitol and poloxamers. The xylitol or poloxamers may be present in a unit dose amount about 1 mg to about 700 mg, such as about 10 mg to about 50 mg, about 50 mg to about 200 mg, about 100 mg to about 400 mg, about 200 mg to about 500 mg, about 50 mg or less, about 50 mg or greater, about 100 mg or greater, about 150 mg or greater, about 200 mg or greater, about 300 mg or greater, about 400 mg or greater, about 500 mg or greater, or about 600 mg or greater. Diluents may include water, distilled water, sterile water, water for injection, sodium chloride, or saline solution, for example. The diluent may comprise an aqueous diluent or non-aqueous diluent. Compositions for nebulization to the lower respiratory tract including a dry powder format may be mixed with a sterile diluent prior to nebulization. In some examples, the sterile diluent is an aqueous diluent, such as sterile water, water for injection, or sterile sodium chloride or saline solution. For example, formulating the composition for administration to the lower respiratory tract may include mixing the dry powder contents of one or more capsules, satchels, or other pharmaceutical containers for holding dry powders with a sterile aqueous diluent. Thus, in one example, the composition prepared for administration may further include a diluent, e.g., as disclosed herein, such as an aqueous diluent, which may comprise or consist of water, distilled water, sterile water, water for irrigation, water for injection, saltwater, sodium chloride (e.g., 0.9%) or saline. The composition may include an active ingredient comprising or consisting of one or both of a beta agonist or an anticholinergic and, optionally, one or more of a steroid, mucolytic, antihistamine, theophylline, sodium citrate, zinc, antifungal drug, antibiotic, antiviral, anti-inflammatory, leukotriene receptor antagonist, or quinine sulfate in amounts described herein. The dry powder may also include one or more inactive ingredients in dry powder format such as poloxamers and/or xylitol. The dry powder ingredients may be mixed with sterile aqueous diluent prior to administration to the lower respiratory tract via nebulization.

In some embodiments, the active agents may be derived from, e.g., obtained from, bulk sources and combined to form the dry powder formulation. The dry powder formulation may be prepared in a dry dosage form suitable for dispensing to a user. The composition may also comprise a unit mixture, dose, or combination thereof prepared from such dry powders, e.g., by addition of the dry powder to a sterile aqueous diluent prior to administration. In some embodiments, the sterile aqueous diluent also includes one or more active or inactive ingredients, such as any of the actives or inactives described herein provided in commercial or compounded pharmaceutical solutions or suspensions, such as vials for injection. The composition may comprise the dry powder compressed to form a tablet or may be provided as a loose powder. The composition may further comprise the dry powder encapsulated to provide a dispensable dosage form comprising an encapsulated unit or unit dose. Prior to administration the composition may be crushed into a powder, when in tablet form, or opened to release the dry powder, when in capsule or another contained form. In a further embodiment, a user may mix the dry formulation, e.g., the contents of a capsule or crushed tablet, with a desired base or diluent liquid configured for nebulization to the lower respiratory tract, e.g., a sterile aqueous liquid such as water or sodium chloride solution.

A method of making the composition may include combining multiple ingredients a mixing. For example, mixing may include shaking or otherwise mixing the combined ingredients, sifting the resulting powder mixture through a fine mesh strainer, mixing the powdered mixture until a homogeneous powder results. A suitable mixer for this purpose is a TURBULA® mixer, which is able to mix powdery substances with differing specific weights and particle sizes. The mixing is generally performed for about one hour or less. The resulting homogeneous mixture can be supplied into pharmaceutical containers, such as encapsulated into a suitable capsule, for example a #00 size capsule. Aliquots may be prepared from the mixture for analysis to ensure accurate mixing and final concentration.

In one embodiment, a method of preparing the pharmaceutical composition for delivery to a target site of the respiratory tract of a subject includes mixing the composition with an aqueous diluent to form a nebulization solution. The nebulization solution dosage form may comprise a unit dose quantity of composition within a suitable volume of the diluent. In various embodiments, the suitable volume is that which is suitable for administration of the composition via nebulization. In one embodiment, the suitable volume is that which is suitable for administration via in a small volume nebulizer, which may be an intranasal nebulizer. Intranasal administration via nebulization of the administration formulation of the composition may efficiently deliver the nebulized composition to the respiratory tract. Once delivered, deposits of the formulation, which may be in a concentrated state, may form on surfaces of the respiratory tract. Delivery of the composition using a nebulizer may enhance delivery efficiency and treatment options by providing flexibility with respect to personalization or customization of treatment. Nebulization may be by any suitable commercially available nebulizer device. In one embodiment, the nebulizer solution is delivered to the lower respiratory tract using a small particle nebulization delivery system. For example, the nebulizer solution dosage form may be formulated for inhalational delivery to the lungs via a small particle size nebulizer, such as a PART or Sinustar™, Omron, or other nebulizer configured to nebulize the dosage form to produce particles or droplets less than 15 microns in size, such as less than 10 microns or less than 5 microns, thereby allowing penetration into the lower respiratory tract, e.g., the lungs. In one embodiment, the small particle nebulization delivery system may be configured to nebulize the formulation to produce small particles or droplets, e.g., having aerosol characteristics, wherein the majority of the particles or droplets formed by the nebulization are less than 5 microns. In some embodiments, 60%, 70%, 80%, or greater of the particles or droplets are less than 5 microns. In various embodiments, nebulization with a small particle nebulizer produces nebulized aerosol particles wherein the majority of particles are less than 10 microns, 8 microns, 5 microns, or 3 microns. In these or other embodiments, the nebulized particles may be produced within a particle size dispersion wherein at least 50%, 60%, 70%, 80%, 90%, or 95% of the particles may be within about 3 microns and about 10 microns, about 3 microns and about 8 microns, about 3 microns and about 5 microns, about 5 microns and about 8 microns, about 5 microns and about 10 microns, or about 8 microns and about 10 microns. Accordingly, a method of administering a nebulizer solution including the composition may comprise using a small particle nebulization delivery system and nebulizing the formulation to form small particles or droplets. The nebulized small particles of the formulation may then be inhaled into the upper airway and deposit thereafter within the lower respiratory tract.

Compared to large particle nebulization delivery systems, small particle nebulization delivery systems deliver a greater fraction of drug to the pulmonary system. This may increase systemic bioavailability of the active agents or drugs. Thus when increased systemic bioavailability is not desirable, e.g., when such bioavailability is linked to unwanted side effects, the formulation may be prepared for and delivered by a large particle nebulization delivery system. In at least one embodiment, treatment of an upper or lower respiratory tract infection comprises nebulizing the nebulizer formulation to produce both small and large particles to target desired respiratory surfaces.

According to one embodiment, the encapsulated dry powder dosage form may be formulated as described above and dispensed to a user, such as a medical professional, patient, assistant, or caregiver. For example, in one embodiment, one or more encapsulated unit doses in a dry powder format may be dispensed to the user. The user may be instructed to prepare the composition for administration just prior to administration. For example, the user may be instructed to combine the unit dose with a diluent, such as a sterile aqueous diluent, for administration of the composition via a nebulizer. The nebulizer may be configured for delivery of the composition to the pulmonary system, e.g., lungs. The nebulizer may be a suitable large or small particle size nebulizer, which, according to some embodiments, may include an intranasal large or small particle nebulizer.

In some embodiments, the composition includes an active ingredient comprising or consisting of a beta agonist in a dry powder format for mixing with a sterile diluent for formulation of a nebulization solution. The beta agonist may be selected from any beta agonist described herein and be provided in any amount or range thereof described herein. In one example, the beta agonist is levalbuterol and/or albuterol. In a further or another example, the beta agonist is provided in a unit dose amount about 0.5 mg to about 2.5 mg, or any range therebetween. For example, the composition may include levalbuterol in an amount about 0.5 mg to about 2.5 mg, albuterol in an amount about 0.5 mg to about 2.5 mg, or both levalbuterol and albuterol each in an amount about 0.5 mg to about 2.5 mg. In a further example, the active ingredient may include one or more additional actives selected from one or more of a steroid, mucolytic, antihistamine, theophylline, sodium citrate, zinc, antifungal drug, antibiotic, antiviral, anti-inflammatory, leukotriene receptor antagonist, or quinine sulfate, such as any of those described herein, in an amount described herein. In one example, the composition includes an additional active selected from one or more of a mucolytic, such as one or more of acetylcysteine, erdosteine, bromheksin, carbocisteine, or guaifenesin, in an amount about 0.5 mg to about 500 mg, such as about 0.5 mg to about 100 mg; steroid, such as one or more of betamethasone, methylprednisolone, fluocinolone, budesonide, diflorasone, desoximetasone, fluocinonide, clobetasol, fluticasone, mometasone, hydrocortisone, or prednisolone, in an amount about 0.25 mg to about 10 mg, such as about 0.5 mg to about 8 mg; antihistamine, such as azelastine, in an amount about 0.5 mg to about 500 mg; theophylline in an amount about 1 mg to about 200 mg; sodium citrate in an amount about 1 mg to about 150 mg, zinc in an amount about 1 mg to about 30 mg; antifungal, such as one or more of amphotericin b, ciclopirox, clotrimazole, econazole, fluconazole, itraconazole, ketoconazole, miconazole, naftifine, nystatin, oxiconazole, ravuconazole, or voriconazole, in an amount about 1 mg to about 100 mg; antibiotic, such as one or more of azithromycin, cefixime, cefotaxime, ciprofloxacin, clarithromycin, clindamycin, colistimethate, doxycycline, erythromycin, gentamicin, levofloxacin, linezolid, nitrofurantoin, or tobramycin, in an amount about 1 mg to about 250 mg; antiviral, such as acyclovir, in an amount about 1 mg to about 100 mg; an anti-inflammatory, such as one or more of salicylate, indomethacin, ibuprofen, diclofenac, flurbiprofen, piroxicam indomethacin, ibuprofen, naxopren, piroxicam, or nabumetone, in an amount about 1 mg to about 60 mg; leukotriene receptor antagonist, such as one or more of montelukast, zafirlukast, or zileuton, in an amount about 0.01 mg to about 20 mg; or quinine sulfate in an amount about 1 mg to about 250 mg. In any of the above examples, the composition may include an inactive ingredient comprising any inactive, such as any of those described herein. In one example, the additional active comprises or consists of the mucolytic acetylcysteine, as described herein. For example, in one embodiment, the composition includes xylitol and/or poloxamer. In a further example, the xylitol and/or poloxamer may be provided in a unit dose amount about 1 mg to about 400 mg. The composition may be in a dry powder format and may be contained within a pharmaceutical container for dry powders, such as a capsule, satchel, or pouch. The dry powder may be mixed with a motorized mixing device, such as a TURBULA®. In one example, the diluent is an aqueous diluent. In one example, the nebulization solution is nebulized for delivery to the lower respiratory tract. In one example, the nebulization solution is nebulized with a small particle nebulizer for delivery to the lower respiratory tract. The small particles may have any particle size or range described herein with respect to small particles. In one example, both small and large particles may be used.

In some embodiments, the composition includes an active ingredient comprising or consisting of a anticholinergic in a dry powder format for mixing with a sterile diluent for formulation of a nebulization solution. The anticholinergic may be selected from any anticholinergic described herein and be provided in any amount or range thereof described herein. In one example, the anticholinergic is ipratropium. In a further or another example, the anticholinergic is provided in a unit dose amount about 0.1 mg to about 1.0 mg, or any range therebetween. For example, the composition may include ipratropium in an amount about 0.1 mg to about 1.0 mg. In a further example, the active ingredient may include one or more additional actives selected from one or more of a steroid, mucolytic, antihistamine, theophylline, sodium citrate, zinc, antifungal drug, antibiotic, antiviral, anti-inflammatory, leukotriene receptor antagonist, or quinine sulfate, such as any of those described herein, in an amount described herein. In one example, the composition includes an additional active selected from one or more of a mucolytic, such as one or more of acetylcysteine, erdosteine, bromheksin, carbocisteine, or guaifenesin, in an amount about 0.5 mg to about 500 mg, such as about 0.5 mg to about 100 mg; steroid, such as one or more of betamethasone, methylprednisolone, fluocinolone, budesonide, diflorasone, desoximetasone, fluocinonide, clobetasol, fluticasone, mometasone, hydrocortisone, or prednisolone, in an amount about 0.25 mg to about 10 mg, such as about 0.5 mg to about 8 mg; antihistamine, such as azelastine, in an amount about 0.5 mg to about 500 mg; theophylline in an amount about 1 mg to about 200 mg; sodium citrate in an amount about 1 mg to about 150 mg, zinc in an amount about 1 mg to about 30 mg; antifungal, such as one or more of amphotericin b, ciclopirox, clotrimazole, econazole, fluconazole, itraconazole, ketoconazole, miconazole, naftifine, nystatin, oxiconazole, ravuconazole, or voriconazole, in an amount about 1 mg to about 100 mg; antibiotic, such as one or more of azithromycin, cefixime, cefotaxime, ciprofloxacin, clarithromycin, clindamycin, colistimethate, doxycycline, erythromycin, gentamicin, levofloxacin, linezolid, nitrofurantoin, or tobramycin, in an amount about 1 mg to about 250 mg; antiviral, such as acyclovir, in an amount about 1 mg to about 100 mg; an anti-inflammatory, such as one or more of salicylate, indomethacin, ibuprofen, diclofenac, flurbiprofen, piroxicam indomethacin, ibuprofen, naxopren, piroxicam, or nabumetone, in an amount about 1 mg to about 60 mg; leukotriene receptor antagonist, such as one or more of montelukast, zafirlukast, or zileuton, in an amount about 0.01 mg to about 20 mg; or quinine sulfate in an amount about 1 mg to about 250 mg. In any of the above examples, the composition may include an inactive ingredient comprising any inactive, such as any of those described herein. In one example, the additional active comprises or consists of the mucolytic acetylcysteine, as described herein. For example, in one embodiment, the composition includes xylitol and/or poloxamer. In a further example, the xylitol and/or poloxamer may be provided in a unit dose amount about 1 mg to about 400 mg. The composition may be in a dry powder format and may be contained within a pharmaceutical container for dry powders, such as a capsule, satchel, or pouch. The dry powder may be mixed with a motorized mixing device, such as a TURBULA®. In one example, the diluent is an aqueous diluent. In one example, the nebulization solution is nebulized for delivery to the lower respiratory tract. In one example, the nebulization solution is nebulized with a small particle nebulizer for delivery to the lower respiratory tract. The small particles may have any particle size or range described herein with respect to small particles. In one example, both small and large particles may be used.

It is to be appreciated that the examples, embodiments, and other descriptions herein with respect to the composition and related methods may specifically exclude any component or ingredient thereof described herein. In some embodiments, the composition does not include other components, such as resins, oils, lipids, water, organic solvents, DMSO, alcohol, fatty acids, inorganic solvents, antibodies, proteins, amino acids, nucleic acids, biological tissues, or biological compounds.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y".

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "about" are intended to include +/−10% of the number modified. For example, a range of about 1 mg to about 10 mg includes 0.9 mg and 11 mg.

The present disclosure may be embodied in other forms without departing from the spirit or essential attributes thereof and, accordingly, reference should be had to the following claims rather than the foregoing specification as indicating the scope of the invention. Further, the illustrations of arrangements disclosed herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of delivering a pharmaceutical composition to the lower respiratory tract, the method comprising:

combining a dry powder with a sterile diluent to formulate a solution or suspension; and nebulizing the solution or suspension, wherein the dry powder comprises a beta agonist or an anticholinergic, wherein the sterile diluent is a sterile aqueous diluent, wherein the dry powder includes the beta agonist and the beta agonist is selected from levalbuterol or albuterol in a unit dose amount of about 0.5 mg to about 2.5 mg, wherein the dry powder further includes xylitol or poloxamers, and wherein the dry powder further includes a mucolytic comprising acetylcysteine in a unit dose amount of about 0.5 mg to about 100 mg.

2. A method of delivering a pharmaceutical composition to the lower respiratory tract, the method comprising:

combining a dry powder with a sterile diluent to formulate a solution or suspension; and nebulizing the solution or suspension, wherein the dry powder comprises a beta agonist or an anticholinergic, wherein the sterile diluent is a sterile aqueous diluent, wherein the dry powder includes the anticholinergic comprising ipratropium in a unit dose amount of about 0.1 mg to about 1.0 mg, wherein the dry powder further includes xylitol or poloxamers, and wherein the dry powder further includes a mucolytic comprising acetylcysteine in a unit dose amount of about 0.5 mg to about 100 mg.

3. The method of claim 2, wherein the dry powder further includes one or more steroids in a unit dose amount of about 0.01 mg to about 8 mg.

4. The method of claim 2, wherein the dry powder further includes one or more antihistamines in a unit dose amount of about 0.1 mg to about 50 mg.

5. The method of claim 2, wherein the dry powder further includes theophylline in a unit dose amount of about 1 mg to about 100 mg.

6. The method of claim 2, wherein the dry powder further includes sodium citrate in a unit dose amount of about 0.5 mg to about 100 mg.

7. The method of claim 2, wherein the dry powder further includes zinc in a unit dose amount of about 0.5 mg to about 30 mg.

8. The method of claim 2, wherein the dry powder further includes one or more antifungal drugs in a unit dose amount of about 0.1 mg to about 100 mg.

9. The method of claim 2, wherein the dry powder further includes one or more antibiotics in a unit dose amount of about 0.5 mg to about 100 mg.

10. The method of claim 2, wherein the dry powder further includes one or more antiviral drugs in a unit dose amount of about 0.1 mg to about 50 mg.

11. The method of claim 2, wherein the dry powder further includes one or more anti-inflammatory drugs in a unit dose amount of about 0.1 mg to about 60 mg.

12. The method of claim 2, wherein the dry powder further includes one or more leukotriene receptor antagonists in a unit dose amount of about 0.01 mg to about 20 mg.

13. The method of claim 2, wherein the dry powder further includes quinine sulfate in a unit dose amount of about 0.5 mg to about 100 mg; or combination thereof.

14. The method of claim 1, wherein the dry powder further includes one or more steroids in a unit dose amount of about 0.01 mg to about 8 mg.

15. The method of claim 1, wherein the dry powder further includes one or more antihistamines in a unit dose amount of about 0.1 mg to about 50 mg.

16. The method of claim 1, wherein the dry powder further includes theophylline in a unit dose amount of about 1 mg to about 100 mg.

17. The method of claim 1, wherein the dry powder further includes sodium citrate in a unit dose amount of about 0.5 mg to about 100 mg.

18. The method of claim 1, wherein the dry powder further includes zinc in a unit dose amount of about 0.5 mg to about 30 mg.

19. The method of claim 1, wherein the dry powder further includes one or more antifungal drugs in a unit dose amount of about 0.1 mg to about 100 mg.

20. The method of claim 1, wherein the dry powder further includes one or more antibiotics in a unit dose amount of about 0.5 mg to about 100 mg.

21. The method of claim 1, wherein the dry powder further includes one or more antiviral drugs in a unit dose amount of about 0.1 mg to about 50 mg.

22. The method of claim 1, wherein the dry powder further includes one or more anti-inflammatory drugs in a unit dose amount of about 0.1 mg to about 60 mg.

23. The method of claim 1, wherein the dry powder further includes one or more leukotriene receptor antagonists in a unit dose amount of about 0.01 mg to about 20 mg.

24. The method of claim 1, wherein the dry powder further includes quinine sulfate in a unit dose amount of about 0.5 mg to about 100 mg.

* * * * *